US006358499B2

(12) United States Patent
Hall-Puzio et al.

(10) Patent No.: US 6,358,499 B2
(45) Date of Patent: Mar. 19, 2002

(54) DEODORANT WITH SMALL PARTICLE ZINC OXIDE

(75) Inventors: Patricia Ann Hall-Puzio, Succasunna; Anne Elisabeth Vickery Gale, Landing; John Carl-Frederick Brahms, Piscataway, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/780,898

(22) Filed: Feb. 9, 2001

Related U.S. Application Data

(60) Provisional application No. 60/183,594, filed on Feb. 18, 2000.

(51) Int. Cl.$^7$ .............................. A61K 7/36; A61K 7/32; A61K 7/00
(52) U.S. Cl. ........................ 424/67; 424/65; 424/400; 424/401
(58) Field of Search ............................ 424/65, 67, 400, 424/401

(56) References Cited

U.S. PATENT DOCUMENTS

| | | |
|---|---|---|
| 4,346,097 A | 8/1982 | Schweiss et al. |
| 4,518,582 A | 5/1985 | Schamper et al. |
| 4,719,102 A | 1/1988 | Randhawa et al. |
| 4,720,381 A | 1/1988 | Schamper et al. |
| 4,722,835 A | 2/1988 | Schamper et al. |
| 4,725,430 A | 2/1988 | Schamper et al. |
| 4,816,261 A | 3/1989 | Luebbe et al. |
| 4,822,602 A | 4/1989 | Sabatelli |
| 4,863,721 A | 9/1989 | Beck et al. |
| 5,122,418 A | 6/1992 | Nakane et al. |
| 5,136,063 A | 8/1992 | O'Lenick, Jr. |
| 5,250,291 A | 10/1993 | Park et al. |
| 5,486,631 A | 1/1996 | Mitchnick et al. |
| 5,871,720 A | 2/1999 | Gutierrez et al. |
| 5,895,644 A | 4/1999 | Albanese et al. |
| 5,939,055 A | 8/1999 | Vu et al. |

FOREIGN PATENT DOCUMENTS

| | | |
|---|---|---|
| EP | 0 260 030 A2 | 3/1988 |
| EP | 0 291 334 A2 | 11/1988 |
| EP | 0 451 002 A2 | 3/1991 |
| EP | 0 512 770 A1 | 11/1992 |
| EP | 0 599 775 A1 | 6/1994 |
| GB | 2 280 111 A | 7/1994 |
| WO | WO 92/19221 | 11/1992 |
| WO | WO 99/59538 | 11/1999 |
| WO | WO 99/59539 | 11/1999 |

OTHER PUBLICATIONS

A. Zombeck, "Novel Formulations Based on Nonaqueous Emulsions of Polyols in Silciones", Oct. 25–25, 1996, pp. 1–12.

Walter Noll, "Chemistry and Technology of Silicones", 1968 by Academic Press Inc., pp. 190–196 and 239–245.

*Primary Examiner*—Shelley A. Dodson
(74) *Attorney, Agent, or Firm*—Rosemary M. Miano

(57) ABSTRACT

This invention comprises a one-phase cosmetic composition which can be made as a stick, gel or cream and which has low residue, low tack and improved fragrance substantivity. The cosmetic compositions are formed by (a) from 0.5–50 weight percent of a dimethicone copolyol ester compound soluble in propylene glycol; (b) from 50–98 weight percent of a gellant/solvent system which comprises a mixture of; (i) 0.5–4.0 weight percent dibenzylidene sorbitol; (ii) 0.05–1.0 weight percent of a co-gellant or structural integrity enhancer; (iii) 0.1–80 weight percent of a polyhydric alcohol solvent; (c) 0.5–10% of a small particle size zinc oxide having a particle size in the range of 20 nanometers–200 microns; and (d) 0.1–3.0% fragrance.

23 Claims, No Drawings

DEODORANT WITH SMALL PARTICLE ZINC OXIDE

This application claims benefit of Provisional application Ser. No. 60/183,594, filed Feb. 18, 2000.

FIELD OF THE INVENTION

This invention relates to low residue deodorants in the form of solid sticks or gels, which are based on dibenzilidene sorbitol (DBS) as a gellant and a polyhydric alcohol such as propylene glycol (PG) as a solvent in combination with a selected dimethicone copolyol ester soluble in propylene glycol (PG). This invention relates to the use of these materials as anti-tack agents in combination with micronized zinc oxide and fragrance in deodorants formulations.

BACKGROUND OF THE INVENTION

Dibenzylidene sorbitol (also called dibenzaldehyde monosorbitol acetal, or dibenzyl monosorbitol acetal or dibenzylidene monosorbitol acetal) and derivatives thereof (such as those which are substituted on one or both of the aromatic rings with a fluorine or methoxy group and those which have the sorbitol portion replaced with other reduced sugars such as xylitol or ribitol as described in U.S. Pat. No. 5,609,855 assigned to Procter & Gamble) (collectively referred to as dibenzylidene sorbitol or "DBS") may be used in various food and cosmetic applications. For cosmetic uses the more interesting ones are those focused on obtaining a translucent or clear product. While dibenzylidene sorbitol is stable in alkaline or neutral media, such compounds are not stable in acidic media. In an acidic environment, such as in the presence of acidic antiperspirant materials, and in the presence of even small amounts of water, the dibenzylidene sorbitol deteriorates and breaks down. Also, the use of DBS sometimes causes problems in the aesthetics of cosmetic products or problems with structural properties. Accordingly, there is a need to find a way to form products containing DBS which are stable and which have acceptable aesthetics.

The use of DBS in an antiperspirant formulation requires the inclusion of polyhydric alcohols such as propylene glycol as a solvent if a clear, transparent product is desired. The high propylene glycol content, when combined with aluminum salts which are included in antiperspirant compositions for wetness control, contribute to undesirable tackiness or a sticky feel for these products when applied to the axilla region of the body. Clear antiperspirant sticks were first formulated with DBS in the late 1970's. Since then there have been continued technical efforts to reduce the negative sensory attributes. Some of these efforts have focused on alternative solvents to replace a portion of the propylene glycol with organic esters known in the art as emollients. This creates a further problem since many of these emollients are either unsafe for personal care products or do not achieve acceptable aesthetics.

For formulating personal care products the incorporation of silicone fluids is known in the art. Silicone fluids such as cyclosiloxanes (for example, DOW CORNING® 244 and 245 Fluids) are used in some major commercial products. Silicone fluids are used because of their low tackiness, superior glide and skin-feel properties. However, silicone fluids are difficult to introduce into DBS based cosmetic stick products such as antiperspirants because they are not good solvents for DBS and they are not readily compatible with propylene glycol and many organic esters or emollients.

Some of the efforts to overcome these problems are described as follows. For example, some efforts have focused on the stability of DBS. United Kingdom Pat. No. GB 2 280 111 assigned to Union Camp Corporation, describes a gel stick composition comprising a dihydric alcohol as a primary solvent, a co-solvent such as low molecular weight polyethylene glycol, water and/or glycerine, a buffering agent and DBS as a gelling agent.

U.S. Pat. No. 4,720,381 to Schamper et al notes stability problems with this approach and itself describes the use of solvents having less reactive hydroxy groups or alcohols with selected chain lengths in a DBS composition.

U.S. Pat. No. 4,816,261 to Luebbe et al describes stable deodorant gel stick compositions comprising DBS with a polar solvent and a coupling agent such as polypropylene glycol ethers of fatty alcohols.

U.S. Pat. No. 4,822,602 to Sabatelli teaches the use of dimethicone copolyols and volatile silicones in clear DBS-based sticks.

U.S. Pat. No. 5,405,605 to Shin teaches anhydrous clear antiperspirant sticks substantially free of lower monohydroxy alcohols which sticks contain dibenzilidene monosorbitol with weak basic organic nitrogen containing compounds as a stabilizing agent.

U.S. Pat. No. 4,518,582 to Schamper, et al discloses an antiperspirant stick composition containing dibenzyl monosorbitol acetal in the presence of acidic antiperspirant-active salts, which composition is stable for extended periods of time at elevated temperatures. The composition contains at least a reactive solvent (such as water, methanol, ethanol, n-propanol, ethylene glycol, 1,2-propylene glycol, 1,3-propylene glycol, etc.), dibenzyl monosorbitol acetal, an antiperspirant-active compound, and a gel stabilizer such as magnesium sulfate, zinc acetate and mixtures thereof. This patent discloses that the stabilizer prevents or retards deterioration of the gelled sticks, especially when exposed to elevated temperatures.

Another patent disclosing stabilizers for solid gel antiperspirant sticks containing an acidic antiperspirant-active compound in the presence of dibenzyl monosorbitol acetal is U.S. Pat. No. 4,719,102 to Randhawa, et al. This patent discloses that the sticks include a solvent which is a small, polar organic compound such as cyclic esters, amides, amines, ketones, ureas, carbamates, sulfoxides and sulfones, and their open chain analogs; a cosolvent such as primary or low molecular weight alcohols and/or glycols; dibenzyl monosorbitol acetal; an antiperspirant-active compound; and a gel stabilizer such as N-(2-hydroxyethyl) fatty ($C_8$–$C_{20}$) acid amides, magnesium sulfate, zinc acetate, acetamide monoethanol amine and hexamethylenetetramine, and mixtures thereof.

U.S. Pat. No. 4,722,835 to Schamper, et al discloses antiperspirant gel stick compositions gelled with dibenzyl monosorbitol acetal and containing an acidic antiperspirant compound as well as a stabilizer such as 1% or less of zinc oxide for the gel. This patent teaches that the compositions include a solvent which is a small, polar organic compound, as discussed previously in connection with U.S. Pat. No. 4,719,102; dibenzyl monosorbitol acetal; an antiperspirant-active compound; and a gel stabilizer such as zinc oxide, calcium acetate, magnesium oxide, calcium carbonate, calcium hydroxide, magnesium carbonate, sodium carbonate, zinc carbonate and potassium carbonate. The basic metallic salt gel stabilizers are said to stabilize the gel, even at high temperatures. U.S. Pat. No. 5,250,291 to Park et al also teaches low levels of zinc oxide as a stabilizer for DBS systems. The use of zinc oxide as a stabilizer is believed to be needed because of the presence of the antiperspirant active.

U.S. Pat. No. 5,490,979 to Kasat et al describes a clear DBS stick comprising guanidine carbonate as the buffer and which is made by a unique processing method.

Other patent documents also disclose antiperspirant sticks gelled with dibenzylidene sorbitol and include stabilizers for the gel. EP Application No. 451 002 A2 discloses a stable, substantially anhydrous and substantially lower monohydric alcohol free, transparent, gelled, antiperspirant composition gelled by dibenzylidene monosorbitol acetal, containing acidic antiperspirants, and utilizing dihydric alcohols containing 3 to 6 carbon atoms as solvents, with the acetal being stabilized against hydrolysis and the formation of benzaldehyde by the presence of a stabilizing amount of a selected organic base, the organic base being a weakly basic, nitrogen-containing, organic compound. EP Application No. 512 770 A1 l discloses a stable, substantially anhydrous and substantially lower aliphatic monohydroxy alcohol free cosmetic composition gelled by dibenzylidene monosorbitol acetal, and containing acidic antiperspirant compounds and utilizing dihydroxy aliphatic alcohols containing 3–6 carbon atoms as solvents, wherein the dibenzylidene monosorbitol acetal gelling agent is stabilized against hydrolysis and the formation of benzaldehyde by the presence of a stabilizing amount of a selected inorganic base, the inorganic base including alkali and alkaline earth metal oxides, hydroxides, carbonates or bicarbonates, and trivalent metallic hydroxides. PCT No. WO 92/19221 discloses solid antiperspirant compositions in gel stick form, having an acid pH, and including (1) an antiperspirant active; (2) a gelling agent selected from the group consisting of substituted and unsubstituted dibenzylidene alditols; (3) a solvent for the gelling agent, preferably including a solvent material selected from the group consisting of monohydric and polyhydric alcohols, and mixtures thereof; and (4) a gelling agent stabilizer, the stabilizer being a basic metallic salt of an acid having a pKa of from about 3.8 to about 6.5 at 25 degrees C., the salt being at least partially soluble in the composition and being selected from the group consisting of $C_4$–$C_6$ dicarboxylate salts, $C_6$–$C_8$ monocarboxylate salts, and substituted or unsubstituted benzoate salts, and mixtures thereof, the gelling agent stabilizer not containing amino or amido functionalities. It is stated that for clear or translucent sticks, the gelling agent stabilizer present in the composition should be fully soluble in the composition, in order to minimize refraction of light.

The foregoing patent documents also disclose methods for forming the disclosed antiperspirant stick compositions containing the antiperspirant materials and gelling agent. In particular, attention is directed to U.S. Pat. No. 4,719,102 and No. 4,722,835. Each of these patents discloses processes of forming the stick compositions, including dissolving the antiperspirant active in one phase and the dibenzyl monosorbitol acetal gellant in another phase. The two phases are then combined and poured into a mold or into the final package. The other components are added to either of the two phases depending on the compatibility of the component with the phases. More phases can be utilized, if desired, by forming a separate solution of some of the components, with the separate phases then being added to either of the two main phases; or all of the phases could be poured together at the end, as, for example, with a multi-stream filling head or an in-line mixer.

There have also been efforts to develop DBS compositions to improve the aesthetics and/or mechanical properties while not sacrificing stability. U.S. Pat. No. 4,346,097 to Roehl discloses a solid translucent gelled antiperspirant composition comprising DBS with an oleaginous compound (such as selected siloxanes, selected esters with an aliphatic character and branched chain hydrocarbons) to reduce stickiness. U.S. Pat. No. 5,725,846 to Vu et al describes a clear gel cosmetic stick which includes a liquid vehicle, an antiperspirant salt dissolved in the liquid vehicle, DBS and one or both of hydroxypropyl cellulose and a chelating agent. The hydroxypropyl cellulose maintains the hardness of the stick. U.S. Pat. No. 5,895,644 to Albanese et al describes a clear gel cosmetic stick which includes a liquid vehicle, an antiperspirant salt dissolved in the liquid vehicle, DBS and the use of selected guars.

U.S. Pat. No. 4,863,721 to Beck et al describes the use of particulate cellulose ether polymers such as hydroxyethyl cellulose in antiperspirant compositions which are substantially free of polar solvents.

European Patent 0 260 030 B1 assigned to Unilever N.V. describes a transparent deodorant stick containing DBS and a thickening agent such as a chemically modified cellulose, polyacrylic acid, and/or polyacrylic acid copolymers and mixtures of the foregoing.

U.S. Pat. No. 4,822,602 to Sabatelli describes cosmetic compositions such as deodorant and antiperspirant sticks comprising (a) water-soluble active; (b) dimethicone copolyol; (c) volatile silicone oil; (d) propylene glycol; (e) C2–C4 monohydric alcohol; (f) water; (g) solidifying agent (such as soap type gel forming agents and DBS); and (h) coupling agent (such as C6–C22 fatty alcohols and propylene glycol ethers of C4–C22 fatty alcohols).

U.S. Pat. No. 4,725,430 teaches a clear or translucent cosmetic stick containing an acidic material (such as antiperspirant salts) and a reactive solvent (for example, various propylene glycols) using DBS as the gelling agent and an N-(2-hydroxyethyl)acetamide as the stabilizing agent.

U.S. Pat. No. 5,302,382 to Kasprzak describes a method of making stable emulsified personal care products which includes the steps of (i) forming an anhydrous silicone mixture having a silicone oil or silicone gum with two silicone oxyalkylene copolymers; (ii) forming an aqueous based pre-emulsified personal care product; and (iii) adding the anhydrous silicone mixture directly to the pre-emulsified personal care product without further emulsification.

U.S. Pat. No. 5,449,519 to Wolf et al describes a cosmetically acceptable composition with keratolytic activity which composition includes a carrier molecule having at least one hydroxyl or amino group.

U.S. Pat. No. 5,531,986 to Shevade et al describes a low residue antiperspirant solid stick containing an antiperspirant active, volatile and nonvolatile silicone materials, dimethicone copolyol and high-melting point and low-melting point waxes.

As described above, it is well known in the art that silicone containing compounds impart good aesthetic characteristics to personal care products. These characteristics include lubricity (glide), conditioning, dry feel and low tack. The addition of a silicone material to a DBS/PG formulation is not easy because of the insolubility of the usual silicone ingredients (for example, cyclomethicone or dimethicone) in propylene glycol.

A recent attempt to incorporate silicone has been published in U.S. Pat. No. 5,871,720 to Albanese et al, where a functionalized silicone was found to provide the good characteristics mentioned above. This technology involves two phases since the silanol used is not soluble in PG. Also, in order to be clear the two phases need to have the same or closely matched refractive indices (RI).

Other references of interest include U.S. Pat. No. 4,472,835 to Schamper et al; Zombeck, A., "Novel Formulations Based on Nonaqueous Emulsions of Polyols in Silicones" (Paper presented at the 19$^{th}$ IFSCC Congress, Sydney, Oct. 22–25, 1996); and Schamper, T., et al, "Acid Stable Dibenzylidene Sorbitol Gelled Clear Antiperspirant Systems", *J. Soc. Cosmet. Chem.*, Vol. 37, pages 225–231 (July/August 1986); Smith, J. M., et al, *J. Mater. Chem.*, 5(11): 1899–1903 (1995).

With reference to zinc oxide, two PCT cases, WO 99/59538 and 99/59539 to The Boots Company PLC, describe compositions having high surface area zinc oxide having a particle size of 0.1–200 microns, which compositions can be used for absorbing sweat and other body liquids or bad breath and body odor, respectively. U.S. Pat. No. 5,122,418 to Shiseido Company Ltd. Teaches a composite powder made with a resin and a coating of, for example, zinc oxide having a particle size of 0.01–1 micron. These powders can be used in deodorants. An example of a hydrophobically treated zinc oxide that is not useful in this invention is described in U.S. Pat. No. 5,486,631 to Siltech, Inc. In view of these references, it is surprising that the fragrance substantivity of the compositions of the present invention is enhanced with the use of formulations that contain the zinc oxide component described below.

There still remains a need, however, to develop cosmetic products made with DBS which are translucent, made as a one phase system, and which provide reduced tack and enhanced fragrance substantivity in the final cosmetic product. Thus, it is an object of the present invention to provide a cosmetic composition which comprises DBS and which provides reduced tack when applied to the skin. It is a further object of the invention to provide cosmetic compositions containing DBS which can be used to form deodorants which are translucent, one phase systems with a silicone compound soluble in propylene glycol. It is yet another object of the invention to provide cosmetic compositions, which enhance the compatibility of DBS in propylene glycol systems that also contain silicone compounds. These and other objects of the invention will be apparent from the following description of the invention.

SUMMARY OF THE INVENTION

This invention comprises a one-phase cosmetic composition, especially a deodorant, which is a stick, gel or cream and which has low tack, low residue and improved fragrance substantivity. The cosmetic compositions are formed by combining the components described below to form a one phase system. These components, all listed in weight percent based on the total weight of the composition, are:

(a) 0.5–50 weight percent of a dimethicone copolyol ester compound soluble in propylene glycol;
(b) 50–98 weight percent of a gellant/solvent system which comprises a mixture of:

(i) 0.5–4.0 weight percent dibenzylidene sorbitol;
(ii) 0.05–1.0 weight percent of a co-gellant or structural integrity enhancer;
(iii) 0.1–80 weight percent of a solvent selected from the group consisting of polyhydric alcohols for example, propylene glycol, dipropylene glycol, tripropylene glycol and tetrapropylene glycol, PPG-10 butane diol, 1,3-butane diol, PEG-6, PPG-425, 2-methyl-1,3-propane diol ("MP Diol") and mixtures thereof, optionally including up to 50 percent of other solvents selected from the group consisting of propylene carbonate, diisopropyl sebacate, methyl pyrrolidone, and ethyl alcohol as a substitute for a portion of the polyhydric alcohol component;

(c) 0.5–10% (particularly 0.5–7.0, and more particularly 0.5–5.0%) of a small particle size zinc oxide, particularly a micronized zinc oxide or a nanoparticle size zinc oxide having a particle size in the range of 20 nanometers-200 microns;

(d) 0.1–3.0% fragrance; and (e) optionally one or more members selected from the group consisting of at least one additional member selected from the group consisting of silicone material; emollients, bacteriostats, coloring agents, etc.

The compositions of this invention are made by combining the components described above in a one phase system to form a gelled composition which may be in the form of a stick, cream or gel. In accordance with the present invention these sticks, creams and gels can be made by combining the materials listed above using conventional mixing techniques.

DETAILED DESCRIPTION OF THE INVENTION

The following and more particular description of the invention more fully explains the cosmetic compositions that can be made.

The dimethicone copolyol esters useful in this invention are those of Formula I:

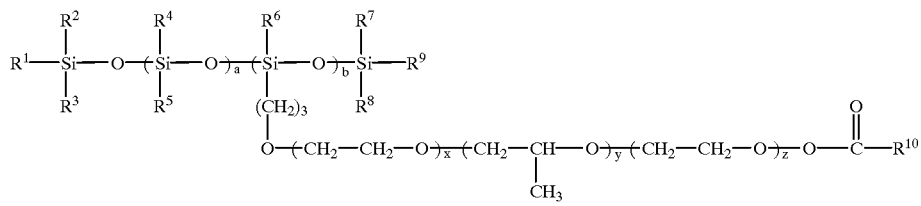

Formula I wherein each of $R^1$–$R^9$ may be the same or different and are each independently selected from the group consisting of $C_1$–$C_4$ straight chain alkyls (especially methyl) phenyl, and substituted phenyl groups wherein the substitution is a member selected from the group consisting of methyl and ethyl;

$R^{10}$ is selected from the group consisting of $C_1$–$C_{20}$ linear and branched chain alkyls particularly $C_4$–$C_{18}$ alkyls, more particularly $C_8$–$C_{16}$ alkyls and especially linear $C_{11}$ (laurate), all with or without unsaturations;

a is a number in the range of 0–500, particularly 0–100, more particularly 1–20, and even more particularly 5–15;
b is a number in the range of 1–100, particularly 1–50, more particularly 1–20, and even more particularly 2–6;
x, y and z are each independently selected to be a number in the range of 0–20, with particular values of x, y, z each being in the range of 0–7, provided that at least one of x, y, and z is not equal to zero. It is to be recognized that a, b, x, y and z are average values (including whole numbers and fractions) and mixtures of compounds with each compound having different values for a, b, $R^1$–$R^9$ and $R^{10}$ may also be used.

In one particular set of compounds of Formula I, none of x, y, or z have a value of zero and each value of x, y, and z has an average value independently selected from the values 2, 3, and 4.

Specific examples of compounds of Formula I include:
(a) linear polydimethylsiloxane where a=10, b=4, x=7, y=z=0, $R^{10}$=$C_{11}$;
(b) linear polydimethylsiloxane where a=10, b=4, x=3, y=2, z=4, and $R^{10}$=$C_{11}$;
(c) linear polydimethylsiloxane where a=10, b=4, x=4, y=2, z=3, $R^{10}$=$C_{11}$;
(d) linear polydimethylsiloxane where a=25, b=10, x=z=0, y=6, and $R^{10}$=$C_{11-17}$;
(e) mixtures of the particular compounds described in parts (a)-(d), and (f) two component mixtures of the particular compounds described in parts (a)–(d) wherein one component is 0.1–99.9% of the composition and the other component is the remainder to 100%.

For each of the groups listed as (a)–(d) above, particular examples of the compounds are when each of the R groups ($R^1$–$R^9$) is selected to be methyl.

For any of the groups (a)–(d), one or more additional silicone fluids may be added, for example in amounts of 0.1–50%. Such additional fluids may be selected from the group consisting of (1) polyalkylene oxide modified polydimethylsiloxanes (for example, products sold under the designations SILWET L-7600, SILWET L-7605, SILWET L-7657); (2) dimethicone copolyols (for example, products sold under the designations SILWET L-7200, SILWET L-7644); and (3) dimethicone copolyol methyl ether (for example, a product sold under the designation SILWET L-7087), where such SILWET products are available from Witco, located in West Virginia.

For the compounds of Formula I to be used with this invention, some of the compounds of Formula I may be obtained from commercial sources and others are described in the literature. A description of selected dimethicone copolyol esters and methods of making such esters used in this invention may be found in the literature, for example, U.S. Pat. No. 5,136,063 assigned to Siltech Inc., which is incorporated herein by reference in its entirety. While this family of compounds is generally named dimethicone copolyol esters, other names for these compounds are silicone fatty esters, silicone waxes. Trade names for such compounds of Formula I include the SILWAX WSL series and are commercially available from Lambent Inc., Norcross, Ga. As noted above, compounds of Formula I can be used with or without additional silicone compounds.

The co-gellant or structural integrity enhancer is selected from the group consisting of hydroxypropyl cellulose, alkyl ester thickeners (for example, PEG-150 pentaerythrityl tetrastearate called CROTHIX® from Croda Chemicals, Parsippany, N.J.), fumed silica (for example, Cab-O-Sil®, from Cabot, Flemington, N.J. Aerosil® from DeGussa, Ridgefield Park, N.J.), waxes such as alkyl methylsiloxanes (for example, AMS-30 (C30–C45 alkyl methicone available from DOW CORNING CORPORATION, Midland, Mich.), selected guars such as an hydroxy $C_3$–$C_4$ alkyl guar having a level of hydroxyalkylation of 0.4–1.5 molar substitution as described in U.S. Pat. No. 5,895,644. Hydroxypropyl cellulose may be used in an amount of 0.05–1.0% by weight based on the total weight of the composition. Other co-gellants may be used in similar amounts, that is, in the range of 0.05–2.0% by weight based on the entire weight of the composition.

Various types of zinc oxide which have small particle sizes can be used in this invention, including treated and non-treated zinc oxide, especially non-hydrophobically treated zinc oxides can be used. One type of zinc oxide is denominated "micronized" and may have a particle size in the range of 0.01–200 microns, especially in the range of 0.01–100 microns. Another type of zinc oxide is characterized as being in the "nanoparticle range" with an example being NANOX™ nano-sized zinc oxide (untreated) from Rheox Inc. (Hightstown, N.J.) and Elementis Specialties (Gent, Belgium). This product has an average particle size of about 60 nanometers with more expansive range being 40–60 or 40–80 nanometers. If treated zinc oxides are used, a pre-mix with a suitable compatibilizing agent should be formed such as using SILWAX materials with a hydrophobically treated zinc oxide.

Known antimicrobials and bacteriostats include bacteriostatic quaternary ammonium compounds such as 2-amino-2-methyl-1-propanol (AMP), cetyl-trimethylammonium bromide, cetyl pyridinium chloride, 2,4,4'-trichloro-2'-hydroxydiphenylether (Triclosan), N-(4-chlorophenyl)-N'-(3,4-dichlorophenyl)urea (Triclocarban) and various zinc salts (for example, zinc ricinoleate). The antimicrobial or bacteriostat can, illustratively, be included in the composition in an amount of 0.01–1.0% by weight, of the total weight of the composition. Triclosan, can illustratively be included in an amount of from 0.01% to about 0.5% by weight, of the total weight of the composition.

Other components used to make the compositions of the invention is the remainder and portion comprising one or more of the following optional ingredients: water, ethanol, emollients, fragrances, and coloring agents.

Emollients useful in this invention (also denominated as "emollient component" here to include a single emollient as well as a mixture of emollients) may be selected from the group consisting of emollient oils such as a liquid mixture of hydrocarbons which are liquids at ambient temperatures (such as petroleum distillates and light mineral oils), mineral oil, peanut oil, sesame oil, avocado oil, coconut oil, cocoa butter, almond oil, safflower oil, corn oil, cotton seed oil, castor oil, olive oil, jojoba oil, paraffin oil, cod liver oil, palm oil, soybean oil, wheat germ oil, linseed oil, and sunflower seed oil; fatty acid esters such as isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate and lauryl lactate; fatty acids such as lauric, myristic, palmitic, stearic, oleic, linoleic, and behenic, acid; fatty alcohols such as lauryl, myristyl, cetyl, isocetyl, stearyl, isostearyl, oleyl, ricinoleyl, erucyl, and 2-octyl dodecanol, alcohols; lanolin and its derivatives such as lanolin, lanolin oil, lanolin wax, lanolin alcohols, lanolin fatty acids, isopropyl lanolate, ethoxylated lanolin, and acetylated lanolin alcohols such as ACETULAN®, a trademark and product of Amerchol Corporation, Edison, N.J.; and hydrocarbons such as petrolatum and squalene.

Particular emollients or emollient component may be selected to reduce wetness. Such emollients may be used to replace all or part of the normally used polyalkylene glycol monobutyl ether. These additional emollients include one or more members from the group consisting of di-n-heptanoylneopentalene glycol ("DNPG"), diisopropyl adipate (also known as bis(1-methylethyl) hexanedioate); dimethicone copolyol wax (for example Dow Coming DC 2501, from Dow Coming Corporation, Midland, Mich.); tetradecyl 2,2-dimethyl propanoate (also called myristyl neopentanoate (for example, DERMOL 145 from Alzo International Inc., Sayreville, N.J.); polyoxypropylene-3-myristyl ether (Promyristyl PM3); polyalkylene glycol monobutyl ether (UCON lubricant 50 HB 100); and (bis(1-methylethyl) hexanedioate (DERMOL DIA). A particular combination of emollients includes polyoxypropylene-3-myristyl ether (Promyristyl PM3); polyalkylene glycol monobutyl ether (UCON lubricant 50 HB 100); and (bis(1-methylethyl) hexanedioate (DERMOL DIA). These emollients may be used in amounts of 0.1–5% to give a total emollient (also referred to as emollient component) addition level of 0.5–10% (total emollient being the polyalkylene glycol monobutyl ether and this additional emollient component, which itself may be one or more of the additional emollients listed here).

A desired feature of the present invention is that a translucent cosmetic composition can be provided. The term "translucent composition", although allowing light to pass through, causes the light to be scattered so that it will be impossible to see clearly objects behind the translucent composition. An opaque composition does not allow light to pass through. Within the context of the present invention, a gel, cream or stick is deemed to be translucent if the maximum transmittance of such light through the sample is between 2% and less than 35%. A gel, cream or stick is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application No. 291 334 A2. Thus, according to the present invention, there are differences between transparent (clear), translucent and opaque compositions.

Particular embodiments of the invention which may be used are sticks having formulations which are at least translucent.

Because of the chemical instability of DBS in the presence of water in low pH media, it is preferred that formulations be essentially anhydrous and contain sufficient buffering agents to keep the pH in the range of 4.0–5.0, however, this is not required and the composition can contain up to 20% water.

Particular compositions according to the present invention include those made by combining in percent by weight based on the total weight of the composition:

(a) 0.5–10% (for example, 0.5–2%) of the dimethicone copolyol esters;
(b) 25–70% of a polyhydric alcohol selected from the group consisting of propylene glycol, dipropylene glycol, tripropylene glycol, tetrapropylene glycol and mixtures thereof;
(c) 1.5–4% (for example 1.65–3%) dibenzylidene sorbitol;
(d) 2.5–7% zinc oxide with a particle size of 40–60 nanometers;
(e) 1–2% fragrance; and
(f) 0.5–10% of an emollient component (one or more emollients).

A second particular embodiment includes:
(a) 1.0–8% (for example 1–3%) of the dimethicone copolyol esters;
(b) 25–70% of a polyhydric alcohol component comprised of at least two polyhydric alcohols selected from the group consisting of propylene glycol, dipropylene glycol, tripropylene glycol, tetrapropylene glycol and mixtures thereof;
(c) 1.5–3% (for example 1.65–1.9%) dibenzylidene sorbitol;
(d) 2.5–3.0% zinc oxide with a particle size of 40–60 nanometers;
(e) 1–2% fragrance; and
(f) 0.5–10% of an emollient component (one or more emollients).

A third particular embodiment includes:
(a) 1–20% (for example, 1–15%) of the dimethicone copolyol esters;
(b) 40–80% of a polyhydric alcohol component comprised of at least two polyhydric alcohols selected from the group consisting of propylene glycol, dipropylene glycol, tripropylene glycol, tetrapropylene glycol and mixtures thereof;
(c) 1.5–3% (for example 1.65–1.9%) dibenzylidene sorbitol;
(d) 2.5–7% (for example 2.5–5.0%) zinc oxide with a particle size of 40–60 nanometers;
(e) 1–2% fragrance; and
(f) 0.5–10% of an emollient component (one or more emollients).

A fourth particular embodiment includes:
(a) 0.5–5% of the dimethicone copolyol esters;
(b) 40–80% of a polyhydric alcohol selected from the group consisting of propylene glycol, dipropylene glycol, tripropylene glycol, tetrapropylene glycol and mixtures thereof;
(c) 1.5–4% (for example, 1.65–3%) dibenzylidene sorbitol;
(d) 2.5–7% (for example 2.5–5.0%) zinc oxide with a particle size of 40–60 nanometers;
(e) 1–2% fragrance; and
(f) 0.5–10% of an emollient component (one or more emollients).

Any of the foregoing formulations can also be made with 1.65–1.9% by weight dibenzylidene sorbitol.

Particular compositions can also be made with any of the foregoing formulations wherein the zinc oxide is selected from:

(a) zinc oxide having a particle size in the range of 40–80 nanometers;
(b) zinc oxide having a particle size in the range of 1–70 microns;
(c) zinc oxide having a particle size in the range of 80–100 nanometers;
(d) zinc oxide having a particle size in the range of 100–1,000 nanometers.

The ingredients described for the invention can be combined by conventional techniques, it being understood that gels use lower amounts of gelling agents than sticks. If a cream is desired, the processing is the same as with a stick or gel but without the heating.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

As noted above, the compositions of the present invention have less tack than conventional cosmetic sticks. Tack can be evaluated by various techniques including the Forearm Flex Test.

Forearm Flex Test—In this test the administrator first over-wraps the test products to hide their identity from the panelists and then gives each sample a code number to hide their identity from the statistician who will analyze the data. These precautions are done to avoid bias of the panelists and the test evaluators. Next, one of two products is applied to one arm at the crease of the elbow and the second product is applied to the same area of the other arm. The two products are applied in a similar manner. Product application is done by either counting the number of strokes or by weighing the products to be tested before and after. Products are applied in random fashion to eliminate left-handed or right-handed biases. The ambient room temperature and humidity are recorded. Using the same control product for every test allows for a comparison between test results for various experimental formulations. The panelists evaluate the tested products for several aesthetic attributes including, but not limited to, wetness, oily/greasy feel, glide, and, most importantly, tackiness/stickiness. The panelists evaluate initial tackiness immediately after a product application and repeatedly at predetermined time intervals for an overall time of 90 minutes. The assessment of tack is made by flexing the arm and judging the adherent forces between contacted skin surfaces. A scale of 1 to 7 is used by each panelist with 1=Not Tacky and 7=Extremely Tacky. The collected data is used to generate a "Tack Profile" which is a plot of Tackiness versus Time. Data analysis using a statistical software package called JMP from SAS Institute (Cary, N.C.) permits identification of products, which are significantly different from the Control sample. The Control is selected to be a competitive benchmark currently in the marketplace, which represents what is believed to be the best commercially available standard. In addition to an analysis of product performance at specific time periods, the performance of the tested sample throughout the 90 minute test period can be made by calculating the area under each curve in the Tack Profile graph and comparing the differences.

The following Examples are given as illustrative of the invention but other modifications may be made by those skilled in the art which are within the spirit and scope of the invention. Unless otherwise noted all amounts are in weight percents. All chemical symbols and scientific abbreviations have their usual and customary meanings and all temperatures are in degrees C. It will also be appreciated by those skilled in the art that preheating of ingredients was done as needed to ensure good mixing.

EXAMPLE 1

As a general procedure for making deodorant sticks, the following procedure can be used. Propylene glycol is weighed out into a main container. Hydroxypropyl cellulose is weighed out and sprinkled into the main container with mixing at room temperature. Mixing is continued for 10 minutes with high speed stirring but no splashing. Tripropylene glycol and a dimethicone copolyol ester (SILWAX WSL) are each weighed out and each added to the main mixture. The DBS is weighed out and gradually added to the mixture with mixing. Mixing is continued at room temperature for 10 minutes with high speed stirring but no splashing. The mixture is heated to a temperature of 110–115 degrees C. with continued mixing until the solution is clear and bright. A suspension of the zinc oxide propylene glycol is made as a separate pre-mix. The zinc oxide pre-mix is heated to a temperature of at least 90 degrees C. Stearyl alcohol is weighed out and added to the main mixture once the mixture is clear. Note that if DC 2501 is used as an emollient, preheating of this material is done to melt it first before addition to the mixture. Mixing is continued until the solution is again clear. The emollient is weighed out, added to the main batch, and mixing is continued until the solution is clear. The batch is cooled to 100 degrees C. The zinc oxide pre-mix is slowly added to the batch and mixed until the mixture is uniform. Fragrance is added to the main batch and the mixture is quickly cooled to 90–92 degrees C. The mixture is then quickly poured into the appropriate containers, for example, containers having dimensions of 3 cm (width at widest part of oval)×6 cm (length of base)×10 cm (height). If an emollient is added to the main batch shortly after the stearyl alcohol addition, the temperature drops close to 100 degrees C., so a slight adjustment may be needed to maintain the temperature at 105 degrees C.

EXAMPLE 2

As a general procedure for making deodorant creams, the following procedure can be used. Propylene glycol is weighed out into a main container. Hydroxypropyl cellulose is weighed out and sprinkled into the main container with high shear mixing at room temperature. Tripropylene glycol and a dimethicone copolyol ester (SILWAX WSL) are each weighed out and each added to the main mixture. The DBS is weighed out and gradually added to the mixture with high shear mixing. Mixing is continued at room temperature for 10 minutes with high shear stirring but no splashing. A suspension of the zinc oxide propylene glycol is made as a separate pre-mix. Note that if DC 2501 is used as an emollient, preheating of this material is done to melt it first before addition to the mixture. Mixing is continued until the solution is homogeneous. The emollient is weighed out, added to the main batch, and mixing is continued until the solution is homogeneous. The zinc oxide pre-mix is slowly added to the batch and mixed until the mixture is uniform. Fragrance is added to the main batch. The mixture is then quickly transferred into the appropriate containers, for example, jars or squeezable tubes.

EXAMPLE 3

The method of Example 1 can be used to make a stick with the following ingredients: 56.75% propylene glycol; 2.0% DBS; 10.00% dimethicone copolyol ester (SILWAX WSL (L7382A); 5% zinc oxide with an average particle size of 60 nanometers (NANOX™) with q.s. propylene glycol; and 1.25% fragrance.

EXAMPLE 4

The method of Example 1 can be used to make a stick with 1% of the dimethicone copolyol ester; 3% zinc oxide (NANOX™ zinc oxide); 51% propylene glycol; 6.25% dipropylene glycol; and 3.75% tripropylene glycol; 2.5% DBS; and 1% fragrance.

We claim:

1. A clear one-phase cosmetic composition formed by combining:
   (a) 0.5–50 weight percent of a dimethicone copolyol ester compound soluble in propylene glycol;
   (b) 50–98 weight percent of a gellant/solvent system which comprises a mixture of:
      (i) 0.5–4.0 weight percent dibenzylidene sorbitol;
      (ii) 0.05–1.0 weight percent of a co-gellant or structural integrity enhancer;
      (iii) 0.1–80 weight percent of a solvent selected from the group consisting of polyhydric alcohols, optionally including up to 50 percent of other solvents selected from the group consisting of propylene carbonate, diisopropyl sebacate, methyl pyrrolidone, and ethyl alcohol as a substitute for a portion of the polyhydric alcohol portion;
   (c) 0.5–10% of a small particle size zinc oxide having a particle size in the range of 20 nanometers–200 microns; and
   (d) 0.1–3.0% fragrance.

2. A cosmetic composition according to claim 1 wherein the dimethicone copolyol esters are those of Formula I:

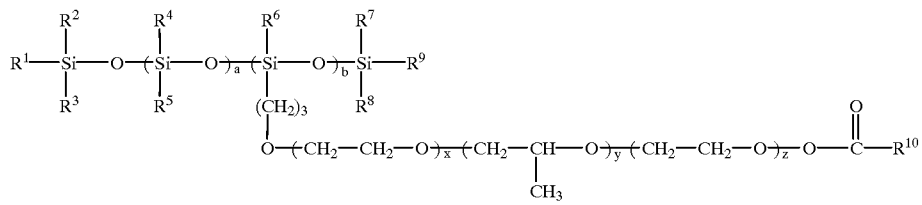

Formula I wherein each of $R^1$–$R^9$ may be the same or different and are each independently selected from the group consisting of $C_1$–$C_4$ straight chain alkyls, phenyl, and substituted phenyl groups wherein the substitution is a member selected from the group consisting of methyl and ethyl;

$R^{10}$ is selected from the group consisting of $C_1$–$C_{20}$ linear and branched chain alkyls with or without unsaturations;

a is a number in the range of 0–500;

b is a number in the range of 1–100; and x, y and z are each independently selected to be a number in the range of 0–20, provided that at least one of x, y, and z is not equal to zero.

3. A cosmetic composition according to claim 2 wherein for the dimethicone copolyol esters of Formula I, each of $R^1$–$R^9$ is methyl.

4. A cosmetic composition according to claim 2 wherein for the dimethicone copolyol esters of Formula I, $R^{10}$ is selected from the group consisting of $C_4$–$C_{18}$ alkyls.

5. A cosmetic composition according to claim 2 wherein for the dimethicone copolyol esters of Formula I, $R^{10}$ is $C_{11}$.

6. A cosmetic composition according to claim 2 wherein for the dimethicone copolyol esters of Formula I, a is a number in the range of 0–100.

7. A cosmetic composition according to claim 2 wherein for the dimethicone copolyol esters of Formula I, a is a number in the range of 1–20.

8. A cosmetic composition according to claim 2 wherein for the dimethicone copolyol esters of Formula I, b is a number in the range of 1–50.

9. A cosmetic composition according to claim 2 wherein for the dimethicone copolyol esters of Formula I, b is a number in the range of 1–20.

10. A cosmetic composition according to claim 2 wherein for the dimethicone copolyol esters of Formula I, x, y and z are each independently selected to be a number in the range of 0–7.

11. A cosmetic composition according to claim 2 wherein the dimethicone copolyol ester of Formula I is a member of the group consisting of those esters of Formula I defined as:
   (a) linear polydimethylsiloxane where a=10, b=4, x=7, y=z=0, $R^{10}$=$C_{11}$;
   (b) linear polydimethylsiloxane where a=10, b=4, x=3, y=2, z=4, and $R^{10}$=$C_{11}$;
   (c) linear polydimethylsiloxane where a=10, b=4, x=4, y=2, z=3, $R^{10}$=$C_{11}$;
   (d) linear polydimethylsiloxane where a=25, b=10, x=z=0, y=6, and $R^{10}$=$C_{11-17}$;
   (e) mixtures of the particular compounds described in parts (a)–(d), and
   (f) two component mixtures of the particular compounds described in parts (a)–(d) wherein one component is 0.1–99.9% of the composition and the other component is the remainder to 100%.

12. A cosmetic composition according to claim 11 wherein each of $R^1$–$R^9$ is methyl.

13. A cosmetic composition according to claim 1 wherein the co-gellant or structural integrity enhancer is selected from the group consisting of hydroxypropyl cellulose, alkyl ester thickeners, fumed silica, and an hydroxy $C_3$–$C_4$ alkyl guar having a level of hydroxyalkylation of 0.4–1.5 molar substitution.

14. A cosmetic composition according to claim 1 wherein the small particle size zinc oxide is either treated or untreated.

15. A cosmetic composition according to claim 1 wherein the small particle size zinc oxide is selected from the group consisting of non-hydrophobically treated zinc oxides.

16. A cosmetic composition according to claim 1 wherein the small particle size zinc oxide has an average particle size in the range of 0.01–200 microns.

17. A cosmetic composition according to claim 16 wherein the small particle size zinc oxide has an average particle size in the range of 0.01–100 microns.

18. A cosmetic composition according to claim 1 wherein the small particle size zinc oxide has an average particle size in the range of 40–80 nanometers.

19. A cosmetic composition according to claim 1 wherein the polyhydric alcohol is selected from the group consisting of propylene glycol, dipropylene glycol, tripropylene glycol, tetrapropylene glycol, PPG-10 butane diol, 1,3-butane diol, PEG-6, PPG-425, 2-methyl-1,3-propane diol, and mixtures of the foregoing.

20. A cosmetic composition according to claim 1 which is made by combining in percent by weight based on the total weight of the composition:
  (a) 0.5–10% of at least one dimethicone copolyol ester;
  (b) 25–70% of a polyhydric alcohol selected from the group consisting of propylene glycol, dipropylene glycol, tripropylene glycol, tetrapropylene glycol and mixtures thereof;
  (c) 1.5–4% dibenzylidene sorbitol;
  (d) 2.5–7% zinc oxide with a particle size of 40–60 nanometers;
  (e) 1–2% fragrance; and
  (f) 0.5–10% of an emollient component.

21. A cosmetic composition according to claim 1 which is made by combining in percent by weight based on the total weight of the composition:
  (a) 1.0–8% of at least one dimethicone copolyol ester;
  (b) 25–70% of a polyhydric alcohol component comprised of at least two polyhydric alcohols selected from the group consisting of propylene glycol, dipropylene glycol, tripropylene glycol, tetrapropylene glycol and mixtures thereof;
  (c) 1.5–3% dibenzylidene sorbitol;
  (d) 2.5–3.0% zinc oxide with a particle size of 40–60 nanometers;
  (e) 1–2% fragrance; and
  (f) 0.5–10% of an emollient component.

22. A cosmetic composition according to claim 1 which is made by combining in percent by weight based on the total weight of the composition:
  (a) 1–20% of at least one dimethicone copolyol ester;
  (b) 40–80% of a polyhydric alcohol component comprised of at least two polyhydric alcohols selected from the group consisting of propylene glycol, dipropylene glycol, tripropylene glycol, tetrapropylene glycol and mixtures thereof;
  (c) 1.5–3% dibenzylidene sorbitol;
  (d) 2.5–7% zinc oxide with a particle size of 40–60 nanometers;
  (e) 1–2% fragrance; and
  (f) 0.5–10% of an emollient component.

23. A cosmetic composition according to claim 1 which is made by combining in percent by weight based on the total weight of the composition:
  (a) 0.5–5% of at lest one dimethicone copolyol ester;
  (b) 40–80% of a polyhydric alcohol selected from the group consisting of propylene glycol, dipropylene glycol, tripropylene glycol, tetrapropylene glycol and mixtures thereof;
  (c) 1.5–4% dibenzylidene sorbitol;
  (d) 2.5–7% zinc oxide with a particle size of 40–60 nanometers;
  (e) 1–2% fragrance; and
  (f) 0.5–10% of an emollient component.

* * * * *